(12) United States Patent
Lowery et al.

(10) Patent No.: US 9,134,736 B2
(45) Date of Patent: Sep. 15, 2015

(54) INTRAVENOUS FLOW RATE CONTROLLER

(71) Applicants: Michael G. Lowery, Wildwood, IL (US); Brian G. Markey, Park Forest, IL (US); James A. McNeely, Buffalo Grove, IL (US)

(72) Inventors: Michael G. Lowery, Wildwood, IL (US); Brian G. Markey, Park Forest, IL (US); James A. McNeely, Buffalo Grove, IL (US)

(73) Assignee: Hospira, Inc., Lake Forest, IL (US)

( * ) Notice: Subject to any disclaimer, the term of this patent is extended or adjusted under 35 U.S.C. 154(b) by 388 days.

(21) Appl. No.: 13/631,422

(22) Filed: Sep. 28, 2012

(65) Prior Publication Data

US 2013/0083191 A1 Apr. 4, 2013

Related U.S. Application Data

(60) Provisional application No. 61/541,709, filed on Sep. 30, 2011.

(51) Int. Cl.
| | |
|---|---|
| *H04N 7/18* | (2006.01) |
| *A61M 31/00* | (2006.01) |
| *G05D 7/06* | (2006.01) |
| *G01F 3/00* | (2006.01) |
| *A61M 5/14* | (2006.01) |
| *A61M 5/168* | (2006.01) |

(Continued)

(52) U.S. Cl.
CPC ........... *G05D 7/0635* (2013.01); *A61M 5/1411* (2013.01); *A61M 5/1689* (2013.01); *G01F 1/56* (2013.01); *G01F 1/72* (2013.01); *G01F 3/00* (2013.01); *G01F 22/00* (2013.01); *G06F 19/3468* (2013.01); *G06T 7/602* (2013.01); *A61M 2205/215* (2013.01); *G06T 2207/20224* (2013.01)

(58) Field of Classification Search
CPC ................. G01F 1/00; G09F 19/3456; A61M 2005/14208; A61M 5/14244
USPC ............................................. 348/135; 604/65
See application file for complete search history.

(56) References Cited

U.S. PATENT DOCUMENTS

| | | | |
|---|---|---|---|
| 4,005,724 A | 2/1977 | Courtot | |
| 4,038,982 A | 8/1977 | Burke | |

(Continued)

FOREIGN PATENT DOCUMENTS

| | | | | |
|---|---|---|---|---|
| BR | PID0704229-9 | 11/2009 | | |
| EP | 000441323 A1 * | 2/1991 | ............. | A61M 5/00 |

(Continued)

OTHER PUBLICATIONS

Specifications for Infusion Pump OT-701, JMS Co., Ltd., Japan, Oct. 2002.

*Primary Examiner* — Dave Czekaj
*Assistant Examiner* — Tsion B Owens
(74) *Attorney, Agent, or Firm* — Brian R. Woodworth

(57) ABSTRACT

Tilting of a drip chamber from its vertical axis during fluid administration can have negative effects upon the accuracy of systems configured for drop counting and/or for volumetric measurement of individual drops passing through the drip chamber. To address these negative effects, in accordance with one embodiment of the present disclosure, a fluid delivery system that measures the flow volume of a fluid delivery system is disclosed, which includes an imaging apparatus that captures a first image of a drip chamber while a drop is falling therein and a second image of the drip chamber with no drop. Portions of each image that are in substantially the same position in each image are subtracted.

20 Claims, 13 Drawing Sheets

(51) Int. Cl.
  *G01F 1/56* (2006.01)
  *G01F 1/72* (2006.01)
  *G01F 22/00* (2006.01)
  *G06T 7/60* (2006.01)
  *G06F 19/00* (2011.01)

(56) References Cited

U.S. PATENT DOCUMENTS

| | | |
|---|---|---|
| 4,048,474 A | 9/1977 | Olesen |
| 4,094,318 A | 6/1978 | Burke |
| 4,105,028 A | 8/1978 | Sadlier |
| 4,173,224 A | 11/1979 | Marx |
| 4,291,692 A | 9/1981 | Bowman |
| 4,328,800 A | 5/1982 | Marx |
| 4,328,801 A | 5/1982 | Marx |
| 4,391,598 A | 7/1983 | Thompson |
| 4,432,761 A | 2/1984 | Dawe |
| 4,432,762 A | 2/1984 | Dawe |
| 4,504,263 A | 3/1985 | Steuer |
| 4,507,112 A | 3/1985 | Hillel |
| 4,525,163 A | 6/1985 | Slavik |
| 4,533,350 A | 8/1985 | Danby et al. |
| 4,551,134 A | 11/1985 | Slavik |
| 4,559,044 A | 12/1985 | Robinson |
| 4,645,489 A | 2/1987 | Krumme |
| 4,668,216 A | 5/1987 | Martin |
| 4,720,636 A | 1/1988 | Benner |
| 4,786,800 A | 11/1988 | Kamen |
| 4,820,281 A | 4/1989 | Lawler |
| 4,857,048 A | 8/1989 | Simons |
| 4,869,722 A | 9/1989 | Heyman |
| 4,936,828 A | 6/1990 | Chiang |
| 5,045,069 A | 9/1991 | Imparato |
| 5,056,992 A | 10/1991 | Simons |
| 5,063,603 A | 11/1991 | Burt |
| 5,186,057 A | 2/1993 | Everhart |
| 5,256,155 A | 10/1993 | Yerlikaya et al. |
| 5,267,980 A | 12/1993 | Dirr, et al. |
| 5,346,466 A | 9/1994 | Yerlikaya et al. |
| 5,389,078 A * | 2/1995 | Zalesky et al. ............. 604/151 |
| 5,788,674 A | 8/1998 | McWilliams |
| 5,899,665 A | 5/1999 | Makino et al. |
| 6,083,206 A | 7/2000 | Molko |
| 6,159,186 A * | 12/2000 | Wickham et al. ............ 604/251 |
| 6,562,012 B1 * | 5/2003 | Brown et al. ................. 604/253 |
| 6,589,792 B1 | 7/2003 | Malachowski |
| 6,599,282 B2 | 7/2003 | Burko |
| 6,617,564 B2 | 9/2003 | Ockerse et al. |
| 6,768,920 B2 | 7/2004 | Lange |
| 6,824,528 B1 | 11/2004 | Faries |
| 6,941,005 B2 | 9/2005 | Lary et al. |
| 2006/0135939 A1 | 6/2006 | Brown |
| 2009/0131861 A1 | 5/2009 | Braig |
| 2009/0227939 A1 | 9/2009 | Mernoe et al. |
| 2010/0077866 A1 | 4/2010 | Graboi et al. |
| 2011/0000560 A1* | 1/2011 | Miller et al. ............ 137/561 R |
| 2011/0077480 A1 | 3/2011 | Bloom et al. |
| 2011/0144595 A1 | 6/2011 | Cheng |
| 2012/0095433 A1 | 4/2012 | Hungerford |

FOREIGN PATENT DOCUMENTS

| | | |
|---|---|---|
| EP | 0441323 | 8/1991 |
| WO | WO 2009 039203 | 3/2009 |
| WO | WO 2009 039214 | 3/2009 |

\* cited by examiner

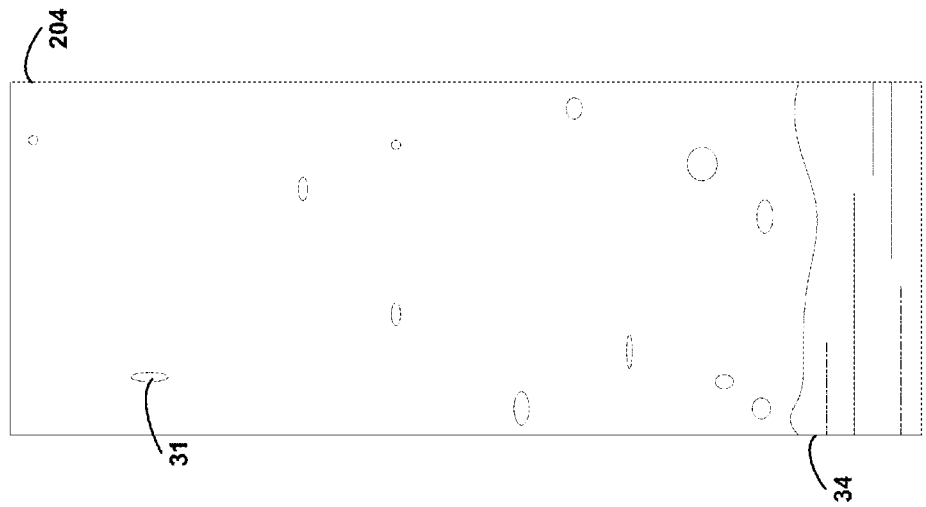
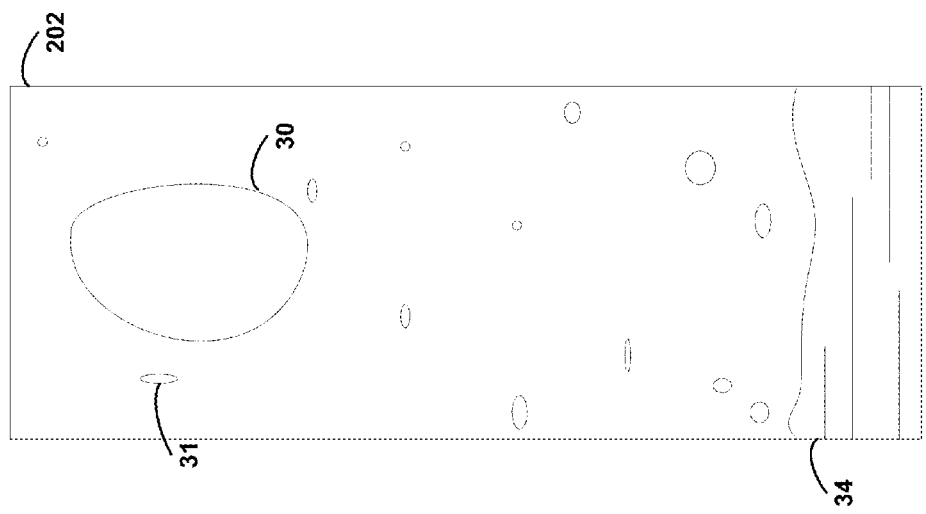

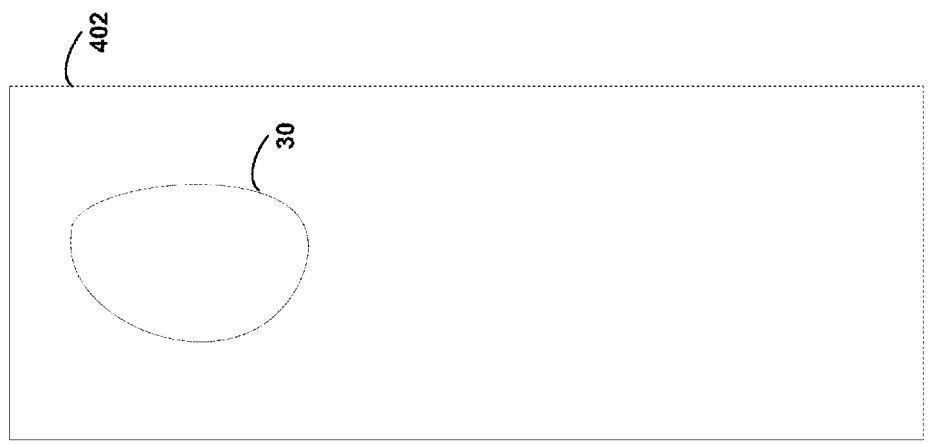

INTRAVENOUS FLOW RATE CONTROLLER

REFERENCE TO RELATED APPLICATION

The present application claims priority to U.S. Provisional Patent Application No. 61/541,709, filed on Sep. 30, 2011, the entirety of which is hereby incorporated by reference.

FIELD OF THE INVENTION

The present disclosure relates generally to systems and methods for fluid delivery control, and more particularly, to intravenous (IV) medicament delivery systems and corresponding methods for flow-rate control and measurement.

BACKGROUND OF THE INVENTION

Intravenous (hereafter "IV") infusion apparatuses are used to deliver a variety of IV solutions to a patient. The IV solution to be delivered to the patient is typically contained in a bottle or flexible container that is fluidly connected to a fluid administration set. The fluid administration set includes a length of tubing designed to run from the bottle or flexible container to a cannula configured for insertion into the patient's blood vessel. Various fluid control devices such as clamps, valves, and/or drip chambers can be included along the length of the administration set. The drip chamber includes a drop former at its upstream end, a substantially transparent chamber through which drops are to fall, and an outlet port at its downstream end. The drop former portion is typically constructed to form drops having a predetermined volume. Many drip chamber manufacturers include details on their products specifying the drop size created in their drip chambers, and in some cases providing a correlation between the number of drops and the volume of fluid passing through the drip chamber.

For example, a drop former may be constructed such that 20 drops equals one milliliter. As the fluid is supplied to the drip chamber from the fluid reservoir, the drop former generates drops of the fluid that fall through the transparent chamber to the outlet port. The flow rate can be determined by counting the number of drops per unit time and then performing a calculation to determine the actual flow rate. For example, if forty drops are counted in a time period of one minute, and the specification of the drip chamber indicates that twenty drops equals one milliliter, then the calculation is that a flow rate of two milliliters per minute exists. Should the actual volume of each drop vary from that specified for the particular drip chamber device, the actual fluid flow rate to the patient will be affected.

The very existence of drops indicates that fluid is flowing in the fluid administration system. The falling drops can be visibly observed in the transparent chamber and counted over a unit of time to calculate the flow rate. The flow rate can be adjusted by a clamp or other device upstream of the drip chamber device, or by downstream means such as an infusion pump or a clamp. If an infusion pump is used, it will engage the administration set downstream of the drip chamber device and can be used to set a flow rate.

Typically, a medication in solution is prescribed at a particular drop rate or volumetric flow rate for a given patient. Maintaining a consistent drop rate or flow rate is desired so that the prescribed treatment is delivered correctly. However, many factors tend to cause the rate to change after it has been initially set. For example, the rate of drop formation is dependent on the head height/pressure of the fluid reservoir. Depletion of the fluid supply will tend to decrease the head pressure on the drop former and will cause a diminution in the rate of drop formation and flow. Vibration or shock may cause the rate controlling clamp to change its adjustment. An obstruction may find its way into the drop former causing the formation of smaller drops thus changing the rate of fluid flow.

Approaches for automating the monitoring process have been provided in the past. Many attempts have been made at providing an automated drop counter. While such systems have proved useful, they do not indicate by direct measurement the actual volume of the fluid detected. They only indicate that a drop has been detected. Such automated systems then use the drop volume specified by the manufacturer of the drip chamber to determine volume, which may not always be accurate.

Another approach for automating the monitoring process includes the inclusion of a mechanism for measuring the volume of drops passing through the drip chamber. For example, an array of photodetectors can be used to determine the size of the shadow of a drop as it passes in front of the detector. However, a variety of factors can interfere with accuracy of these systems, including the presence of condensation or splashed droplets on the interior wall of the drip chamber. Tilting of the drip chamber from its vertical axis may also affect the accuracy of the volumetric calculation by changing the distance between the photodetectors and the drops flowing through the drip chamber.

Accordingly, the inventors have identified a need in the art for a fluid control system that accommodates the variability inherent in the medication delivery environment, such as a hospital or clinic.

SUMMARY

Disclosed herein are fluid control systems and corresponding methods. More particularly, in accordance with one embodiment, an apparatus is provided and includes a cradle configured to receive a drip chamber, a valve configured to receive a length of tubing and to control a rate of fluid flow through the length of tubing, and a flow rate determination element configured to determine a flow rate of fluid passing through the drip chamber. The flow rate determination element includes camera for imaging activity within the drip chamber, a computing device, a memory storage coupled to the computing device, and a set of software instructions stored in the memory storage which when executed by the computing device causes the apparatus to carry out functions. Such functions include detecting a presence of a drop of fluid falling within the drip chamber, in response to the detecting, triggering the camera to capture a first image of the drip chamber with the drop falling therein, capturing a second image of the drip chamber with no drop falling therein, subtracting from the first image portions of the second image that appear in substantially the same position in each of the first and second images in order to create a drop image, and determining a volume of the drop based on the drop image.

In accordance with another embodiment, a method is provided and includes detecting a presence of a drop in a drip chamber, in response to the detecting, capturing a first image of the drip chamber and the drop falling therein, capturing a second image of the drip chamber with no drop falling therein, subtracting from the first image any portions of the second image that appear in substantially the same position in both the first and second images in order to create a drop image, determining a volume of the drop based on said drop image, repeating the preceding steps for successive detected drops over a predetermined period of time, and summing the determined volumes of successive detected drops and dividing the sum by the predetermined period of time to provide a flow rate.

The foregoing summary is illustrative and is not intended to be in any way limiting. In addition to these illustrative aspects, embodiments, and features described above, further aspects, embodiments, and features will become apparent by reference to the figures and the following detailed description.

BRIEF DESCRIPTION OF THE DRAWINGS

Various examples of the disclosed system and corresponding method are described herein with reference to the following drawings, wherein like numerals denote like entities:

FIGS. 2A and 2B illustrate example images of a drip chamber, in accordance with an embodiment;

FIG. 4 illustrates further example image processing, in accordance with an embodiment;

DETAILED DESCRIPTION

The present disclosure is directed to systems and methods configured to provide enhanced flow measurement and flow control in IV administration systems.

Figure 1:
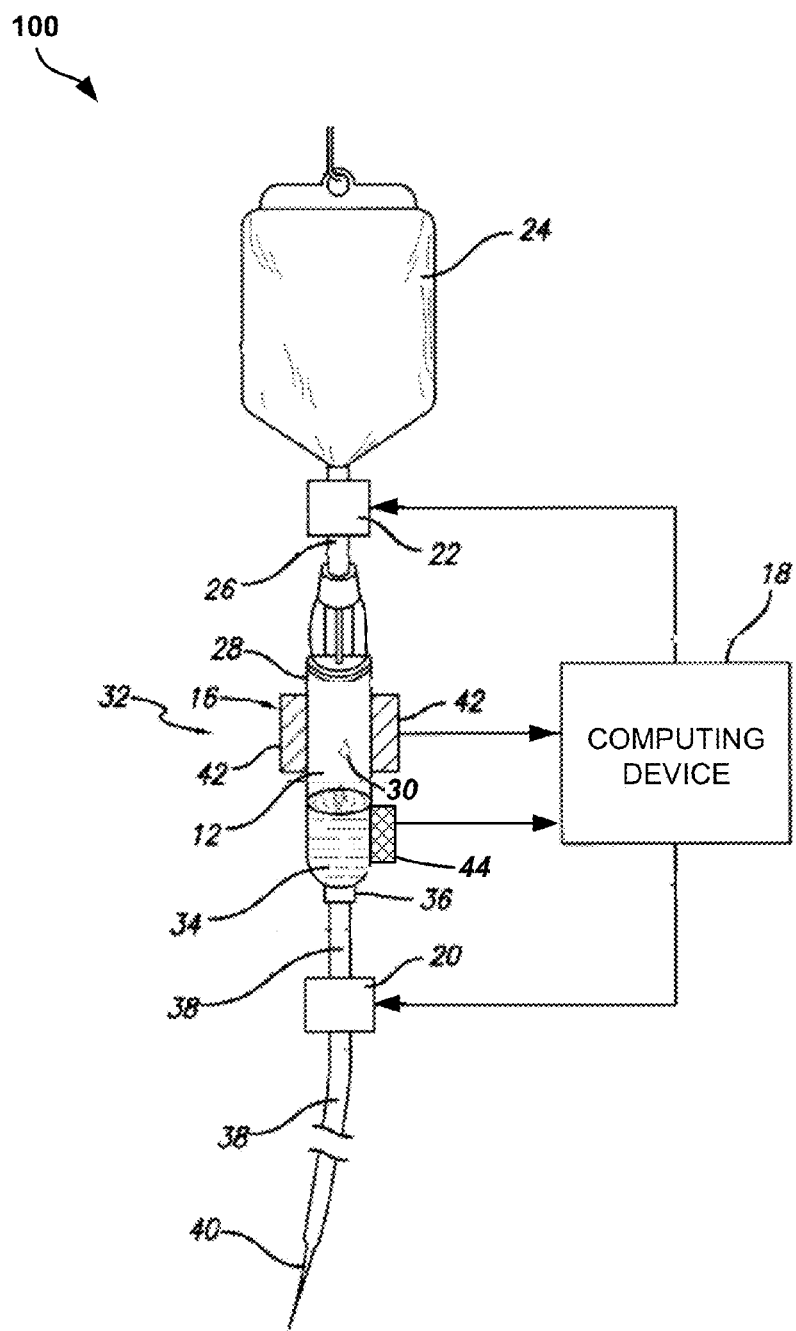
FIG. 1 illustrates an example fluid delivery system, in accordance with an embodiment.

FIG. 1 illustrates an example of a fluid delivery system 100 that can be used in conjunction with an intravenous flow rate controller system constructed in accordance with the present disclosure. It will be appreciated that IV administration sets are well-known in the medical field and that the system 100 described herein is merely intended to be exemplary. As depicted, system 100 includes a container 24. Container 24 can be a bottle, a flexible IV solution container, or any other type of reservoir suitable for containing an IV solution. Container 24 is constructed such that an IV solution contained therein can be accessed for delivery to a patient. For example, container 24 can include an outlet port 22 having a pierceable closure. The pierceable closure is constructed of a material that allows it to receive a spike therethrough such that a substantially fluid-tight seal is created about an exterior wall of the spike at the point that it passes through the pierceable closure. The spike defines a fluid flow channel that is, in turn, in fluid communication with a first end of tubing 26.

Second end of tubing 26 is in fluid communication with drip chamber 12. Drip chamber 12 includes a wall defining an interior chamber. The wall is preferably constructed of a substantially transparent material such as a plastic that allows for visualization of fluid flow through drop chamber 12. Drop former 28 is positioned at a first end of drop chamber 12 in fluid communication with the second end of tubing 26. Drop former 28 is constructed such that it creates discrete droplets of IV solution as the solution flows through tubing 26 into drip chamber 12. Outlet port 36 is positioned at a second, downstream end of drop chamber 12.

Tubing 38 is fluidly connected to outlet port 36 and is constructed to deliver IV solution leaving drip chamber 12 directly or indirectly (i.e., through additional IV administration sets) to a patient. In cases where tubing 38 is configured to delivery IV solution directly to a patient, a cannula 40 can be provided at the distal end of tubing 38. Cannula 40 is of known construction and can be configured for insertion into the circulatory system of a patient.

An IV flow rate controller system in accordance with the present disclosure is generally depicted at 18, 20 and 22 in FIG. 1. In one embodiment, the flow rate controller system includes computing device 18 and at least one flow control device 20/22. Flow control device 20, for example, is positioned downstream of drip chamber 12 and is typically configured to restrict to varying degrees the size of the flow channel defined by tubing 38, thereby controlling the flow of IV solution therethrough. Flow control device 20 may be an electrically controlled clamp or valve that opens to permit flow or closes to restrict flow in tubing 28 in response to an electrical signal described in greater detail below. In one embodiment, flow control device 20 is a piston that can be moved relative to tubing 28 such that the piston pushes inwardly on a wall of tubing 28, thereby reducing the cross-sectional size of the fluid flow path defined through tubing 28 in order to reduce the flow rate of IV solution through tubing 28. In this embodiment, the piston of flow control device 20 can also be moved relative to tubing 28 such that the degree to which the piston depresses tubing 28 is decreased, thereby increasing the cross-sectional size of the fluid flow path defined through tubing 28 and increasing the flow rate of IV solution therethrough. Flow control device 20 preferably is constructed such that it can provide relatively small, incremental increases and decreases to the cross-sectional size of the fluid flow path defined by tubing 28, thereby enabling IV flow rate controller system to provide precise control over flow through fluid delivery system 100.

In some alternate embodiments, the flow controller system includes a second flow control device 22 positioned upstream of drip chamber 12 as depicted in FIG. 1. Flow control device 22 may be included as an addition to flow control device 20, or perhaps in place of flow control device 20. The structure and operation of flow control device 22 may be the same as described above with respect to flow control device 20. For example, flow control device 22 may be an electrically controlled clamp or valve, such as the type discussed above with respect to flow control device 22. Alternatively, flow control device 20 may be an electrically controlled pump (e.g., a volume infusion pump). Upon reception of an appropriate electrical signal, the pump may actuate to force fluid through tubing 38 and into cannula 40. Other suitable approaches may be used as well.

In accordance with one embodiment of the present disclosure, IV flow rate controller system also includes a drip sensor 16 configured to detect when a drop 30 passes through drip chamber 12. In one embodiment, drip sensor 16 is a capacitive sensor and includes two electrically conductive metal plates 42. Plates 42 may be incorporated within the walls of drip chamber 12 or may be positioned external to drip chamber 12, such as by mounting plates 42 on a housing associated with the infusion delivery system, as described below. Plates 42 generally define a capacitor and are electrically coupled to a computing device 18. Computing device 18 may be at least one analog measuring circuit and/or at least one digital microcontroller. An example computing device is described below with respect to FIG. 13. Computing device 18 may provide excitation voltage for the plates 42, and may also continually or periodically measure the voltage across the plates 42.

Computing device 18 in conjunction with drip sensor 16 may operate to detect when a drop is falling within drip chamber 12. For example, when the drip sensor 16 is a parallel plate capacitor, the existence of a drop 30 between plates 42 disturbs the electric field that exists between the plates 42. This disturbance may act to change the capacitance of the plates 42, which can be measured by system 18. In at least one embodiment, for example, computing device 18 applies to plates 42 an oscillating voltage signal having a particular frequency (e.g., about 100 MHz). The oscillating voltage signal has a particular resonant frequency that is a function of the capacitance of plates 42. When a drop 30 falls between the plates 42, the resonant frequency (as measured by computing device 18) changes as a result of the change in capacitance between the plates 42. Computing device 18 may recognize this resonant frequency change and record the change as a "drop event." A drop event may refer to one or more drops falling within the drip chamber 12.

In at least one embodiment, computing device 18 records a drop event if the resonant frequency change is greater than a predefined (or otherwise determined) threshold frequency change (e.g., about 10 MHz). If computing device 18 recognizes a resonant frequency change less than the threshold frequency change, computing device 18 may interpret such a change to be noise (e.g., a drop causing a splash-up or medical personnel handling the device).

Other suitable methods for detecting a drop event may be used as well, such as infrared (IR) light, ultra-violet (UV) light, or radio-frequency (RF) emitter/detector combinations. For example, IR LED emitters may be configured to emit at least one IR light beam through the drip chamber. IR LED detectors may be configured to detect the emitted IR light through the drip chamber. Computing device 18 may include or be coupled with one or both of the emitters and detectors to measure the detected light and determine, based on the detected light, whether a drip is falling within the drip chamber. For example, in some embodiments, computing device 18 records a drop event when the IR beam is broken by a falling drop. Other suitable methods for using emitter/detector combinations for detecting drops and drop volumes are possible as well.

Any number of various emitter/detector combinations may be used as well. For example, in some embodiments, multiple emitter/detector pairs (e.g., ten emitter/detector pairs) are positioned substantially vertically along the drip chamber. Each emitter/detector pair in a column may be positioned some distance apart in the general vertical direction (e.g., by about 2 millimeters). Generally, a detector is configured to detect only the light from its complimentary emitter. In addition, more than one column of emitter/detector pairs may be used, including for example, two columns. Other suitable combinations of IR LED emitters and detectors can be used as well.

Notwithstanding the specific type of drip sensor used, the computing device 18 generally keeps track of how many drop events occur in some unit of time (e.g., one minute) in order to determine a dosage rate. This may be advantageous for health care institutions that prefer to deliver drugs on a drop/minute (or some other unit of time) basis.

In an alternative embodiment, computing device 18 is preprogrammed with an average volume value of a typical drop. Computing device 18 may multiply that number by the preprogrammed volume value to determine a dosage rate. For instance, computing device 18 may be preprogrammed to use about 0.05 milliliter as the drop volume. If the drip sensor 16 detects, for example, one-hundred drops in a time period of one minute, computing device 18 may determine the dosage rate to be five milliliters per minute. The computing device 18 may store this dosage rate for future use or display the dosage rate on a graphical user interface (not shown) for viewing by medical personnel. Those skilled in the art will realize that these values are merely example values and any suitable values may be used.

In accordance with at least one embodiment, some infusion delivery systems include a volume-determination element for a more accurate calculation of the dosage rate. Such systems may be advantageous for health care institutions that prefer to deliver drugs on a mL/hour basis (or some other unit of measurement).

For example, in one embodiment, the infusion delivery system 100 is associated with an imaging apparatus (not shown in FIG. 1) to facilitate drop volume determination. The imaging apparatus may include at least one camera to capture an image of the drop 30 as the drop falls within the drip chamber 12.

Figure 13:
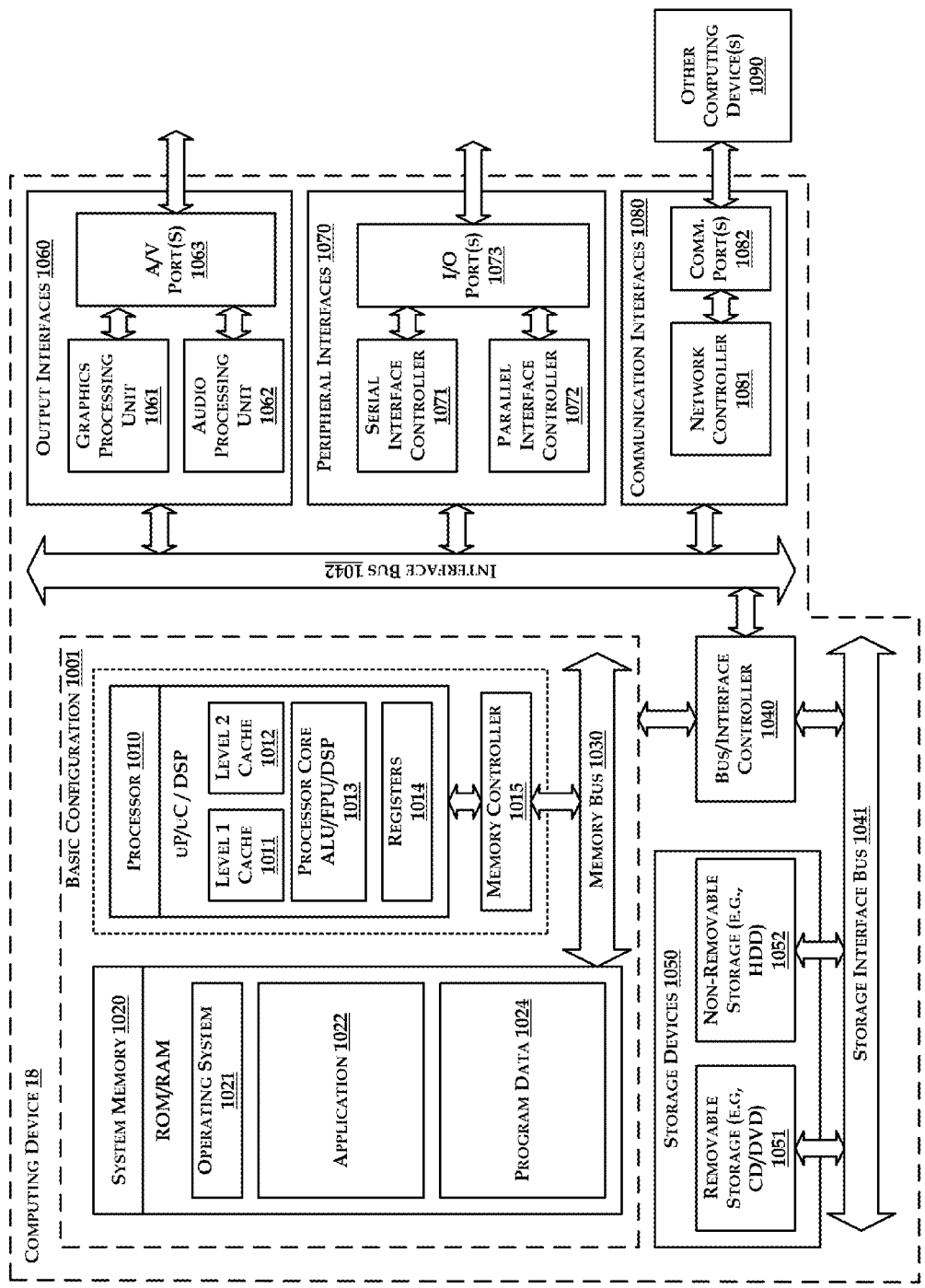
FIG. 13 is a block diagram illustrating an example computing device, in accordance with an embodiment.

The imaging apparatus may be associated with or include various image-processing circuitry, which, in at least one embodiment, takes the form of one or more of the computing devices described herein with respect to FIG. 13. Generally, the image processing circuitry employs various techniques to estimate, from a 2-dimensional image of drop 30, the volume of drop 30. Computing device 18 may use drop volumes determined by this imaging apparatus alone or in combination with drop volumes determined by other means, such as by determining a resonant frequency change and/or a looking up a preprogrammed drop volume to calculate the dosage rate.

FIG. 2A is an illustration of an example image 202 that may be captured by the imaging apparatus. Image 202 may encompass an image of drop 30, part of a pool of solution that resides at the downstream end 34 of drip chamber 12, and one or more "splash effects" 31. Splash effects refer to portions of the solution that stick to a sidewall of drip chamber 12 and are brought about by a drop 30 falling into the downstream pool 34 and creating a splash.

In one embodiment, the image processing circuitry and associated software may process image 202 to identify drop 30. To determine an estimated volume of drop 30, the image processing circuitry (e.g., a processor) may utilize known techniques to identify which pixels of image 202 constitute drop 30 and count those pixels. The circuitry may also computationally rotate the shape of drop 30 about a vertical axis to determine a 3-dimensional shape and a corresponding equation relating the volume (in pixels) of the 3-dimensional shape to the number of pixels in the 2-dimensional image of drop 30. Image processing circuitry may use a preprogrammed ratio of pixels-to-volume (e.g., 100 pixels per 0.01 milliliters), which may be based on various factors, such as the distance of camera lens from the drip chamber, the type and shape of the camera lens, etc. Thus, if a computed pixel-volume of drop 30 is 2431 pixels, image processing circuitry may associate such a drop as having an estimated volume of 0.2431 milliliters. Of course, these are merely example volumes and ratios and any suitable volume or ratio may be used. Computing device 18 may use drop volumes estimated in this manner in place of (or in conjunction with) the preprogrammed drop volume to calculate the dosage rate.

The splash effects 31 may contribute to erroneous drop volume computations if the splash effects 31 appear too close to the drop in the image. When this happens, the image processing circuitry may treat nearby splash effects 31 as being part of the drop 30, and thus, the surface area (as measured in pixels) may be computed as being larger than the actual drop 30. To address this potential erroneous volume computation, the imaging apparatus may employ a "double image technique" to subtract out any splash effects, in accordance with one alternative embodiment of the present disclosure.

Utilizing the double image technique, the imaging apparatus captures a first image 202 of the drip 30 falling within the drip chamber 12. The imaging apparatus may wait for a predetermined amount of time, and upon expiration of the predetermined amount of time, capture a second image 204 of the drip chamber 12 without the drip 30, as illustrated in FIG. 2B. In the second image 204, drop 30 fell and mixed with pool 34, whereas the splash effects 31 remained in relatively the same position in both images. In an alternative embodiment, image 204 may be captured before image 202 is captured. In such an embodiment, the imaging apparatus may capture image 204, which does not contain drop 30. The imaging apparatus may then wait until a drop event is detected, and upon detection of the drop event, capture image 202. Alternatively, the imaging apparatus may wait a predetermined amount of time, and upon expiration of the predetermined amount of time, capture image 202. Other examples of capturing images are possible as well.

Once the images are captured, the image processing circuitry may compare both images 202 and 204 to determine the portions of the image that appear in substantially the same position in both images. The image processing circuitry may then remove from one (or both) images, the determined portions appearing in substantially the same position in both images.

Figure 3B:
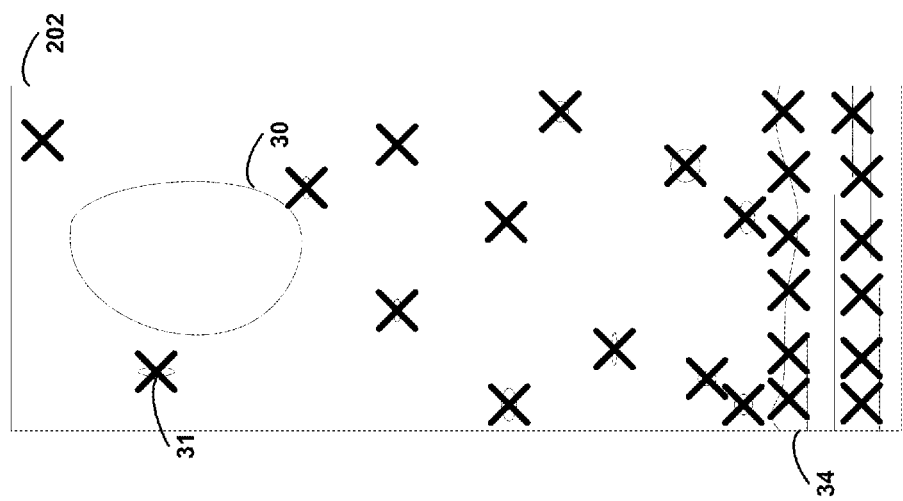
FIGS. 3A and 3B illustrate example image processing, in accordance with an embodiment.
Figure 3A:
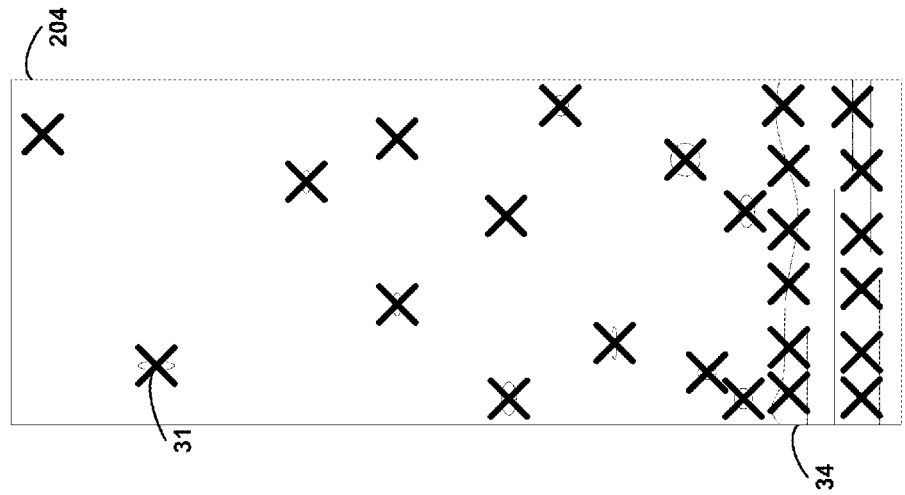

For example, FIG. 3A illustrates example image 202 and FIG. 3B illustrates example image 204, where each image includes an "X" overlapping portions of the image that appear in substantially the same position in both images. Associated image processing circuitry and software may subtract (i.e., remove) these portions from each image. For example, FIG. 4 illustrates an example image 402, which results from subtracting from image 202 the portions of the image that appear in substantially the same position in images 202 and 204. Associated image processing circuitry and software may use image 402 in the manner described above, to estimate the volume of drop 30. Using image 402 to calculate the volume of drop 30 rather than using image 202 may help avoid erroneous volume determinations that may arise because of the splash effects.

In one embodiment, the imaging apparatus includes a camera utilizing a lens that produces substantially similar size images of the drops regardless of how far away from the drip chamber the camera is. Such a camera configuration may provide for a more robust imaging apparatus because the fluid delivery system can be manufactured allowing broader tolerances yet still produce accurate drop volume calculations.

In order to capture an image while the drip is falling within the drip chamber, computing device 18 may utilize drip sensor 16 to recognize when a drop 30 is falling within the drip chamber 12. As described above, drip sensor 16 is typically configured to cause computing device 18 to record a drop event when a drop is present within the drip chamber. Computing device 18 may use recordation of a drop event as a "trigger" to cause an imaging apparatus to capture an image of the drip chamber and falling drop 30. Such a trigger may take the form of at least one electrical signal supplied to the imaging apparatus, for example. In response to receiving the trigger, the imaging apparatus may capture an image of the drip chamber 12 and drop 30.

In embodiments in which the drip sensor 16 is two parallel plates, the trigger may take the form of a measureable resonant frequency change. In such embodiments, the imaging apparatus is typically positioned such that the one or more cameras are substantially perpendicular to the plates 42. On the other hand, in embodiments in which the drip sensor 16 is an IR LED emitter/detector combination (or other similar light-detection apparatus), the trigger may take the form of detection of the light beam being broken. Other suitable triggers are possible as well and usually depend on the type of drip sensor used.

Notwithstanding the specific implementation used to detect drops falling through drip chamber 12, one or more parts of drip sensor 16, plates 42, the imaging apparatus, and computing device 18 may be collectively referred to as a "drop-detection element." And notwithstanding the specific implementation used to estimate the volume of a particular drop 30 falling through the drip chamber 12, one or more parts of drip sensor 16, plates 42, the imaging apparatus, and computing device 18 may also be collectively referred to as a "volumetric-determination element."

Figure 5:
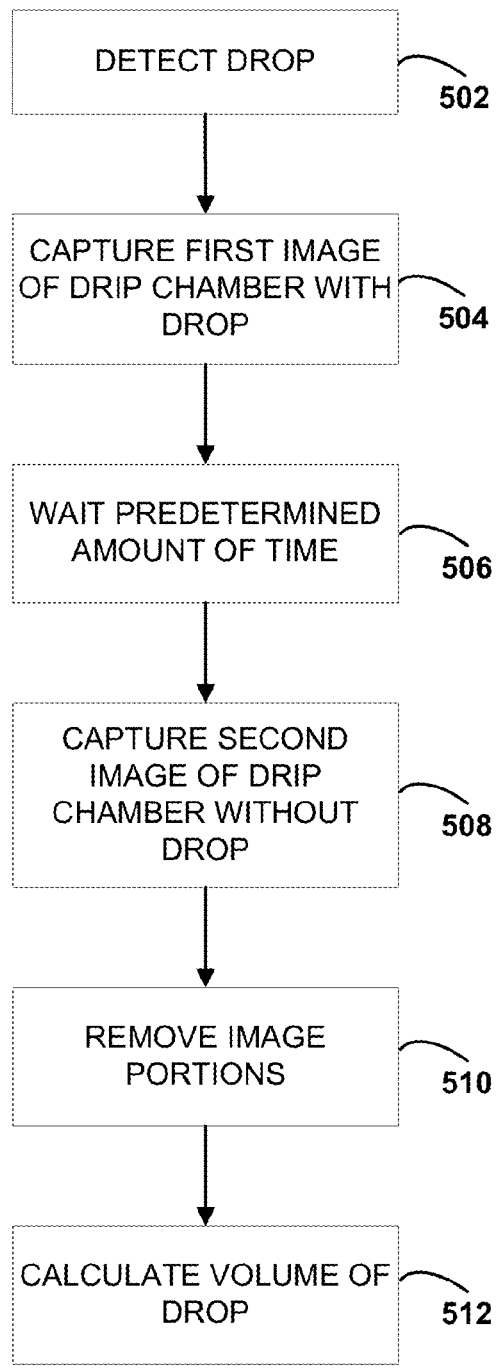
FIG. 5 is a flow diagram illustrating an example method, in accordance with an embodiment.

FIG. 5 is a flow diagram that depicts an example drop volume determination operation that may be performed by one or more of the fluid delivery system 100, computing device 18, and/or imagining apparatus, all collectively referred to as "the system." The example methods may include one or more operations, functions, or actions as illustrated by one or more of blocks 502, 504, 506, 508, 510, and/or 512. Those skilled in the art will understand that the flow diagram depicted in FIG. 5 (as well as other flow diagrams discussed herein) illustrate functionality and operation of one possible implementation of present embodiments. In this regard, each block of each flow diagram may represent a module, a segment, or a portion of program code, which includes one or more instructions executable by a processor for implementing specific logical functions or steps in the process. The program code may be stored on any type of computer readable medium (e.g., computer readable storage medium or non-transitory media), for example, such as a storage device including a disk or hard drive. In addition, each block may represent circuitry that is wired to perform the specific logical functions in the process. Alternative implementations are included within the scope of the example embodiments of the present application in which functions may be executed out of order from that shown or discussed, including substantially concurrent or in reverse order, depending on the functionality involved, as would be understood by those reasonably skilled in the art.

Referring to FIG. 5 at block 502, the system detects that there is a drop falling within the drip chamber. As discussed above, the system may employ drip sensor 16 to make this detection. In some embodiments, drip sensor 16 transmits a trigger signal to the system in response to detecting the drop falling within the drip chamber.

At block 504, in response to the detection of the drop falling within the drip chamber, the system captures a first image of the drip chamber with the drop falling therein. In some embodiments, the imaging apparatus captures this first image in response to receiving the trigger signal from the drip sensor 16.

At block 506, the system waits a predetermined amount of time. In some embodiments, the system waits an amount of time sufficient for the drop that was imaged at block 504 to fall all the way through the drip chamber, but not so long that a next drops begins to fall. By way of example, such a time may be 300 milliseconds; however, other suitable times may be used as well.

At block 508, upon expiration of the predetermined amount of time, the system captures a second image of the drip chamber; however, in this second image, there is no drop falling therein. This second image may be compared with the first image to determine which portions are in substantially the same position in both images.

At block 510, the system compares the first image and the second image to determine which image portions are in substantially the same position in both images. The system removes such portions from the first image. Typically, after this removal operation, the only pixels that remain in the first image are that of the drop. This may help reduce erroneous drop-volume calculations because portions of the image that do not define the drop are removed and will not be accidently included in a volume calculation.

At block 512, the system calculates the volume of the drop. As discussed above, the system may carry out this calculation in any number of suitable ways. For example, the system may determine the number of pixels that define the drop and calculate the volume of the drop based on a preprogrammed ratio of pixels-to-volume. Alternatively, the system may computationally rotate the drop about a vertical axis and calculate the volume of the computationally-rotated shape. The system may use the calculated volume of the drop, and calculated volumes of each drop thereafter, to estimate delivered dosage rates.

In at least one embodiment, computing device 18 is electrically coupled to one or both of the flow control devices 20, 22 (i.e., the "valve") and is operable or configured to provide to the valve various electrical signals for controlling the valve. For instance, a first type of electrical signal (e.g., a 5 Volt signal) provided to the valve may cause the valve to open and consequently permit more solution to flow in the fluid delivery system. Opening the valve may increase the volume of drops flowing through drip chamber 12, and/or increase the rate of drops flowing through drip chamber 12, each of which may cause the measured dosage rate to increase. Likewise, a second type of electrical signal (e.g., a 1.5 Volt signal) provided to the valve may cause the valve to close and consequently restrict solution flow in the system. Closing the valve may decrease the volume of drops flowing through drip chamber 12, and/or decrease the rate of drops flowing through drip chamber 12, each of which may cause the measured dosage rate to decrease. Closing and/or opening the valve may be referred to as "regulating" the fluid flow in the fluid delivery system 100. Further, a third type of electrical signal (e.g., a 0 Volt signal) provided to the valve may cause the valve to stay in relatively the same position (i.e., not closed and not open). Not closing and not opening the valve may be referred to as "holding" the valve or "preventing the valve from changing positional states." Those skilled in the art will realize that these are merely example electrical signals, and computing device 18 and the valve may be configured to use any type of electrical signal to open, close, or hold the valve.

In at least one embodiment, computing device 18 engages in a feedback loop designed to control the valve and regulate fluid flow in the system 100 based on the calculated dosage rate. For example, computing device 18 may measure the dosage rate according to one or more techniques described above, and adjust the valve (e.g., open or close the valve) based on a comparison of the measured dosage rate to a preprogrammed dosage rate (sometimes referred to as a "threshold" or "desired" dosage rate). The preprogrammed dosage rate may be entered into computing device 18 by a medical technician, for example. The computing device 18 may periodically, or continually, compare the measured dosage rate to the preprogrammed dosage rate. When the measured dosage rate is less than the preprogrammed dosage rate, computing device 18 may provide to the valve an appropriate electrical signal to cause the valve to open a threshold amount. As mentioned, causing the valve to open may increase the volume of each given drop, or may increase the rate of drops flowing through the system, or both. When the measured dosage rate is greater than the preprogrammed dosage rate, computing device 18 may provide to the valve an appropriate electrical signal to cause the valve to close a threshold amount. As mentioned, causing the valve to close may decrease the volume of each given drop, or may decrease the rate of drops flowing through the system, or both.

In some embodiments, computing device 18 may open (or close) the valve a specific threshold amount regardless of how much less (or more) the measured dosage rate is than the preprogrammed dosage rate. For instance, computing device 18 may open the valve the same amount for measured dosage rates that are 0.01 milliliter/minute less than the preprogrammed dosage rate or 0.1 milliliter/minute less than the preprogrammed dosage rate. Alternatively, computing device 18 may open the valve an amount commensurate with the difference between the measured dosage rate and the preprogrammed dosage rate. For instance, computing device 18 may open the valve 10 times wider for a measured dosage rate that is less than the preprogrammed dosage rate by 0.1 milliliter/minute as compared with 0.01 milliliter/minute. Other suitable techniques for adjusting the valve based on measured dosage rate may be possible as well.

Some fluid delivery systems (e.g., system 100) are used in environments that tend to cause at least part of fluid delivery system to tilt or swing back and forth, such as inside an ambulance or with a patient being transported throughout a medical facility. When the drip chamber 12 is swinging or is in a tilted position, for instance, drops, such as drop 30 may not flow directly from the upstream end 28 to the downstream end 34. Rather, drops may come into contact with one of the sidewalls of drip chamber 12 before flowing though to downstream end 34. When flowing down the sidewall, drip sensor 16 may not detect the drop and consequently, computing device 18 may not record a drop event. For instance, if drop 30 flows down the side wall, the drop 30 may not cause a large enough disturbance in the electrical field produced by plates 42 to be detected as a drop event by computing device 18. In fluid delivery systems utilizing other methods of drop detection (e.g., IR beam detection methods), drops flowing down the sidewall may similarly result in failed drop detection and missed drop events.

As a result of missed drop events, computing device 18 may calculate an erroneous dosage rate. For instance, if computing device 18 misses five drops out of every twenty, computing device 18 may underestimate the dosage rate by 25%. In turn, computing device 18 may cause the valve to open (in an effort to increase the dosage rate), when in actuality the computing device should have left the valve state the same, or possibly closed the valve to decrease the dosage rate. Erroneously opening the valve may cause too high of a dosage rate delivered to the patient, which can be dangerous.

To address these types of situations, in at least one embodiment, the fluid delivery system 100 may include a tilt detection element or mechanism 44 to detect when at least part of the fluid delivery system 100 is tilted, swinging, or in motion. The tilt detection element 44 may be embedded in or near any portion of fluid delivery system 100 (e.g., drip chamber 12), and may be electrically coupled with or integrated in computing device 18. In some embodiments, the tilt detection element 44 is a 3-axis micro-machined accelerometer, such as those manufactured by Freescale Semiconductor, Inc. Other similar devices now known, or later developed, may be used as well.

In at least one embodiment, the tilt diction element 44 may be arranged to provide a first type of electrical signal (e.g., a 5 Volt signal) to computing device 18 when at least part of the fluid delivery system 100 is in a "tilted state," and provide a second type of electrical signal (e.g., a 1.5 Volt signal) to computing device 18 when at least part of the fluid delivery system 100 is not in a "tilted state." A "tilted state" may refer to any condition in which a part of the fluid delivery system 100 is in a position tending to cause missed drop events and/or an erroneous dosage rate determination. In at least one embodiment, the fluid delivery system 100 is in a tilted state when the whole (or at least part of) fluid delivery system 100 is moving (e.g., being wheeled down a hallway). In at least one embodiment, the fluid delivery system 100 is in a tilted state when at least part (e.g., drip chamber 12) is swinging back and forth, or is tilted at some predefined angle from approximately vertical (e.g., 15 degrees from approximately vertical). Thus, the tilt detection element 44 may include various additional detection elements (e.g., an angular orientation detection element, a swinging detection element, and/or a motion detection element) in order to detect each of these conditions. The tilt detection element 44 may be arranged to detect, and consequently inform computing device 18 of, each of these conditions and perhaps others that may potentially cause missed drop events and/or an erroneous dosage rate determination.

Figure 6:
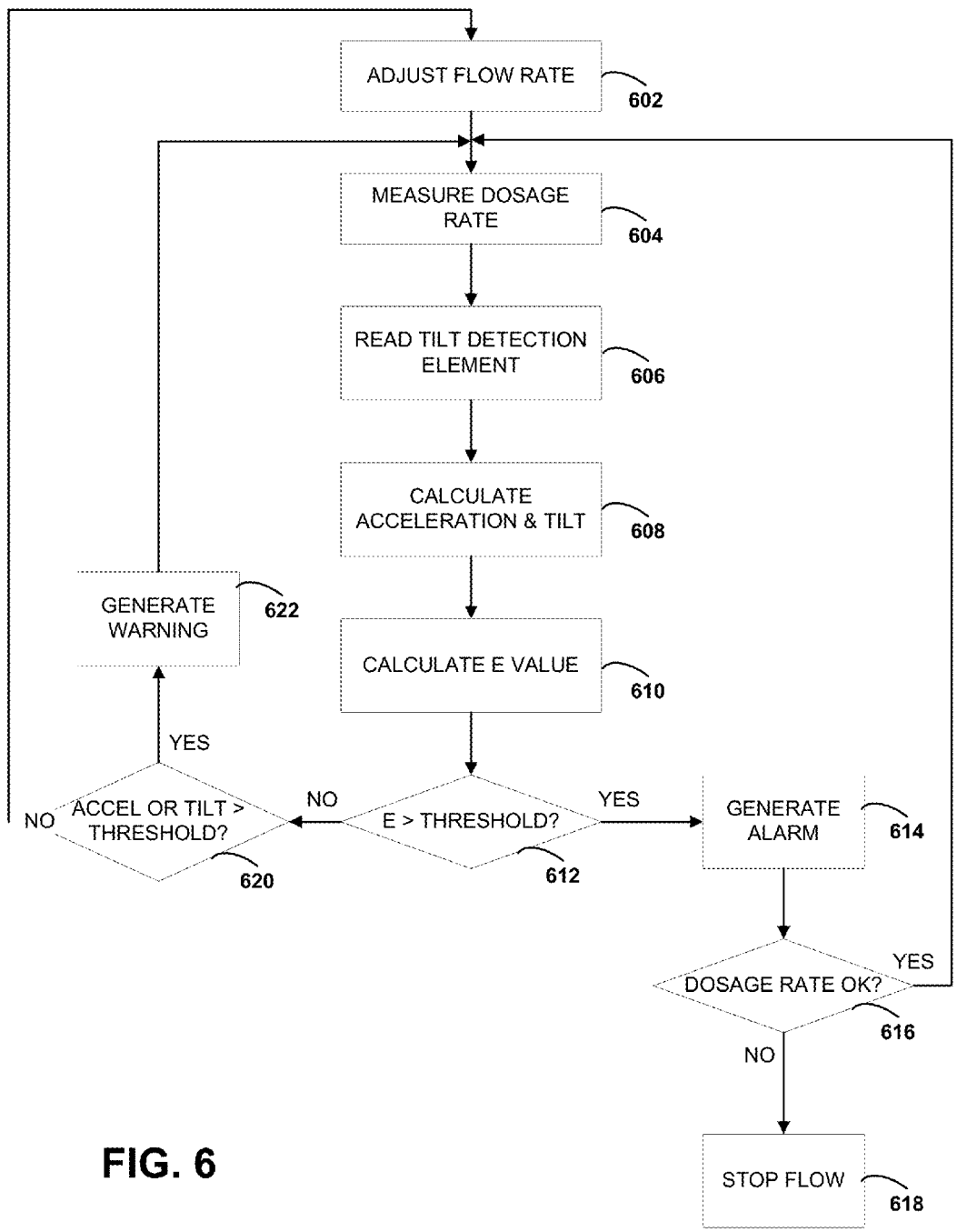
FIG. 6 is another flow diagram illustrating another example method, in accordance with an embodiment.

FIG. 6 is a flow diagram that depicts an example tilt detection and flow control method that may be performed by one or more of the fluid delivery system 100, computing device 18, the tilt detection element 44, and/or imaging apparatus, all collectively referred to as "the system." The example methods may include one or more operations, functions, or actions as illustrated by one or more of blocks 602, 604, 606, 608, 610, 612, 614, 616, 618, 620, and/or 622.

Description of the flow diagram begins at block 606 where the system reads the tilt-detection element. It at least one embodiment, reading the tilt-detection element includes receiving at least one electric signal from an accelerometer. For example, the system 18 may receive an $A_X$ signal, which is indicative of tilt or acceleration in a first direction, an $A_Y$ signal, which is indicative of tilt or acceleration in a second direction, and an $A_Z$ signal, which is indicative of tilt or acceleration in a third direction. These signals may be voltage signals or current signals. In either case, the magnitude of such signals is usually directly proportional to the magnitude of acceleration or tilt in each respective direction.

At block 608, the system calculates acceleration and tilt based on the reading of the tilt detection element in block 606. For example, in at least one embodiment, the system processes the $A_X$, $A_Y$, and $A_Z$ to quantify the instantaneous magnitude and direction of motion and tilting. Typically, if the net magnitude of acceleration equals about 1G (or about 9.8 meters per second-squared), then the device is substantially stationary and the system calculates the tilt angles for analysis. If the net magnitude of acceleration is different than 1 G, the three signals are analyzed to determine device motion.

At block 610, the system calculates an alarm condition parameter, referred to as "E" for simplicity. E is calculated anew during each iteration of the flow control method depicted in FIG. 6. $E_i$ refers to the calculated E value for a most recent iteration of the flow control method, whereas $E_{i-1}$ refers to the calculated E value for the previous iteration of the flow control method. In one embodiment, E ranges between 0.0 and 1.0 and is given generally by the following expression:

$$E_i=(1-P)*E_{i-1}+dE_i.$$

P is a weighting constant given by the expression:

$$P=2/(1+N_E).$$

$N_E$ is a number of data points used to calculate the weighting constant P. Essentially, $N_E$ is analogous to the number of data points used in a standard moving-average equation. Larger values of $N_E$ reduce P, which subsequently dampens the rate of change of E over time. Thus, $N_E$ may be chosen such that it optimizes the response rate of E for triggering alarms, as will be described further herein. In one embodiment, the system has a data sampling speed of 100 samples/second (i.e., the system iterates through the flow control method depicted in FIG. 6 one hundred times per second) and uses a time window of 120 seconds. This yields an $N_E$ value of 12,000 data points. Other values are possible as well.

The $dE_i$ parameter takes on a value between 0.0 and 1.0. It is set to a value of 0.0 when, as determined at block 608, the calculated amount of acceleration and tilt does not exceed a pre-established threshold. It is set to the value of P when, as determined at block 608, the calculated amount of acceleration and tilt exceeds the pre-established threshold. Thus, from one data point to the next, E increases slightly when the calculated amount of acceleration and tilt exceeds the threshold (because $dE_i=P$), whereas, from one data point to the next, E decreases slightly when the calculated amount of acceleration and tilt does not exceed the threshold (because $dE_i=0$).

In some embodiments, it may be advantageous to reset E to zero after a sufficient amount of time has passed (e.g., 30 seconds) in which the calculated acceleration and tilt have remained below their preset thresholds. Employing this reset technique may reduce the carry-over of non-zero E values to future data points. In turn, this may reduce nuisance alarms during future tilt events.

After the calculation of E at block 610, the system makes a determination of whether the E value exceeds a threshold value. One example threshold value for E is 0.5, but any value between 0.0 and 1.0 may be used. Threshold values are typically pre-programmed into computing device 18; however, in some embodiments, healthcare personnel may change the threshold value. For example, a threshold value of 0.75 is relatively resistant to tilt events (i.e., it takes a lot of tilting to raise an alarm), whereas a threshold value of 0.25 is particularly sensitive to tilt events (i.e., it does not take very much tilting at all to raise an alarm). Different situations may call for different thresholds values, such as the environment of the system, the type of drug being administered, the availability of healthcare personnel to respond to alarms, etc.

If, at block 612, E is greater than the threshold value, an alarm condition is generated at block 614. In at least one embodiment, an alarm condition is an audible, visual, or some other type of indication designed to inform healthcare personnel that there has been excessive tilting and/or acceleration upon the fluid delivery system. Generally, the alarm will prompt healthcare personnel to inspect the fluid delivery system and take corrective action to remedy the excessive tilting and/or acceleration.

Upon generating an alarm, the system determines at block 616 if the measured dosage rate is within a user-specified range despite the alarm condition. If the measured dosage rate is within an allowable range, then the process proceeds to block 604 and the flow of fluid is not adjusted. However, if the measured dosage rate is not within an allowable range, the flow is stopped at block 618. As described above, flow may be stopped by appropriately actuating flow control device 20/22. Stopping flow may protect the patient from potentially incorrect medication flow rates during periods when the dosage rate cannot be accurately measured, if at all (due to the tilt condition). To resume flow, typically healthcare personnel would resolve the tilt/motion condition and resume flow manually.

Referring back to block 612, if E is not greater than the threshold value, the process proceeds to block 620 where the system determines whether calculated acceleration and tilt (at block 608) exceed some warning threshold. If no, the process proceeds to block 602. If yes, the system generates a warning condition at block 622. Generally, a warning condition is an audible, visual, or some other type of indication designed to inform healthcare personnel that some acceleration and tilting have occurred but it is not so excessive as to cause an alarm condition. The healthcare personnel may choose to respond before the situation progresses to an alarm condition. If the system generates a warning condition at block 622, the process then proceeds to block 604 bypassing the adjustment operation at block 602. This helps prevent an erroneous adjustment operation stemming from an erroneous dosage rate measurement during a warning condition.

At block 602, the system adjusts the flow rate (e.g., by opening or closing the valve, as discussed above) until the measured dosage rate is within allowable limits. Details of this operation are discussed above.

At block 604, the system measures and/or calculates the dosage rate. In some embodiments, the system does so by employing a combination of operations carried out by at least one of the drip sensor 16, the imaging apparatus, and the computing device 18, as discussed above.

Figure 7:
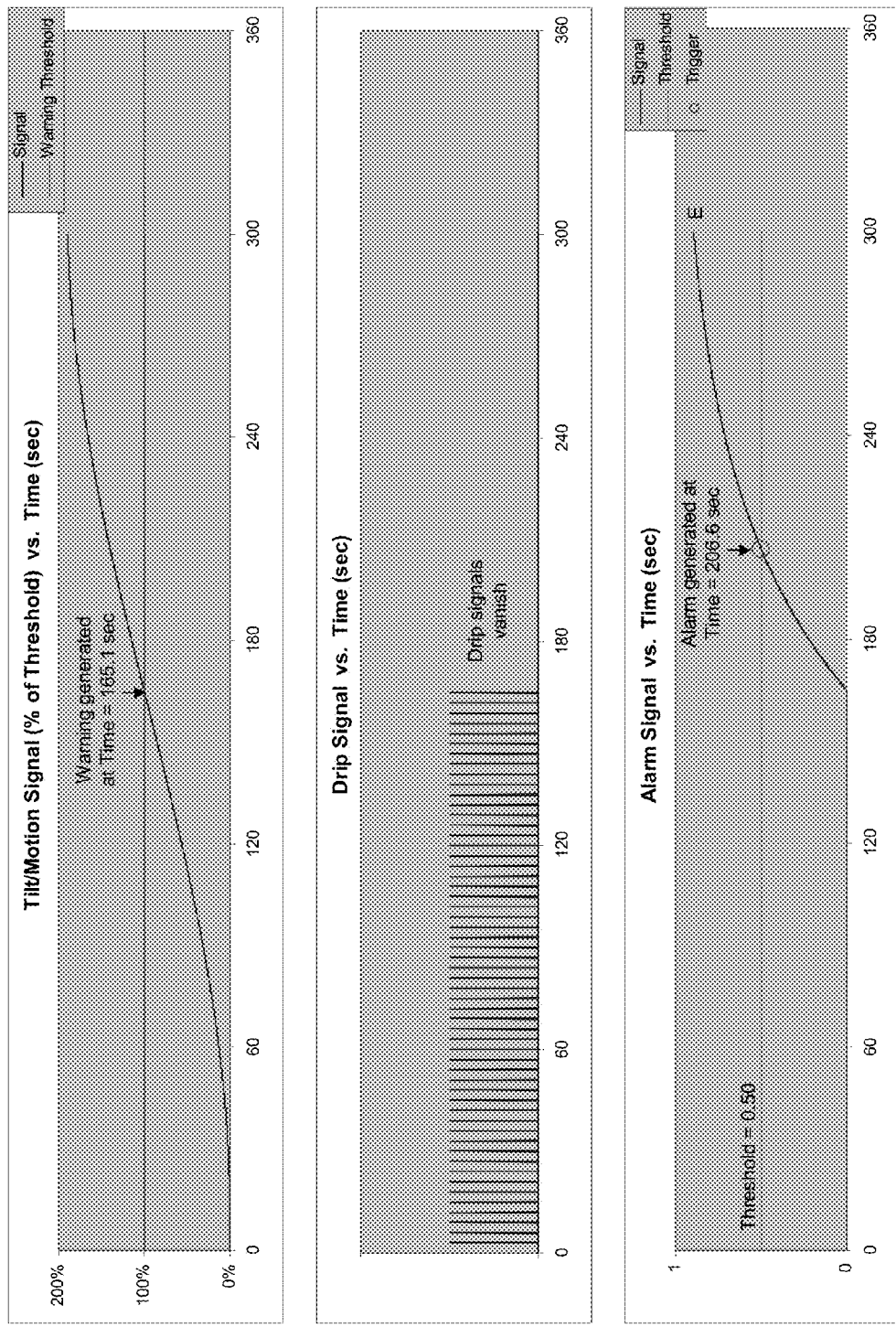
FIG. 7 shows three graphs depicting an example tilt/motion situation, in accordance with an embodiment.
Figure 8:
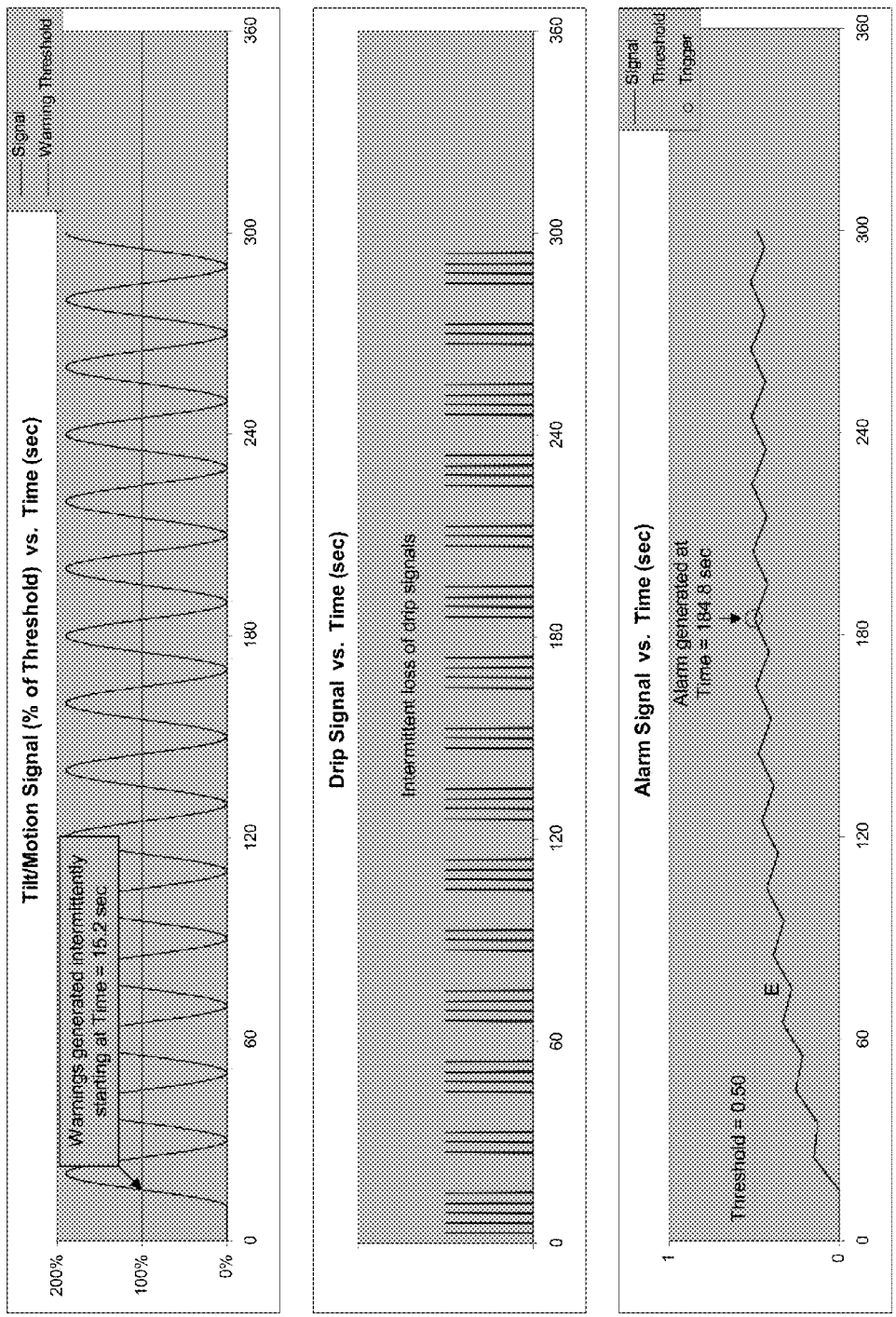
FIG. 8 shows another three graphs depicting another example tilt/motion situation, in accordance with an embodiment.
Figure 9:
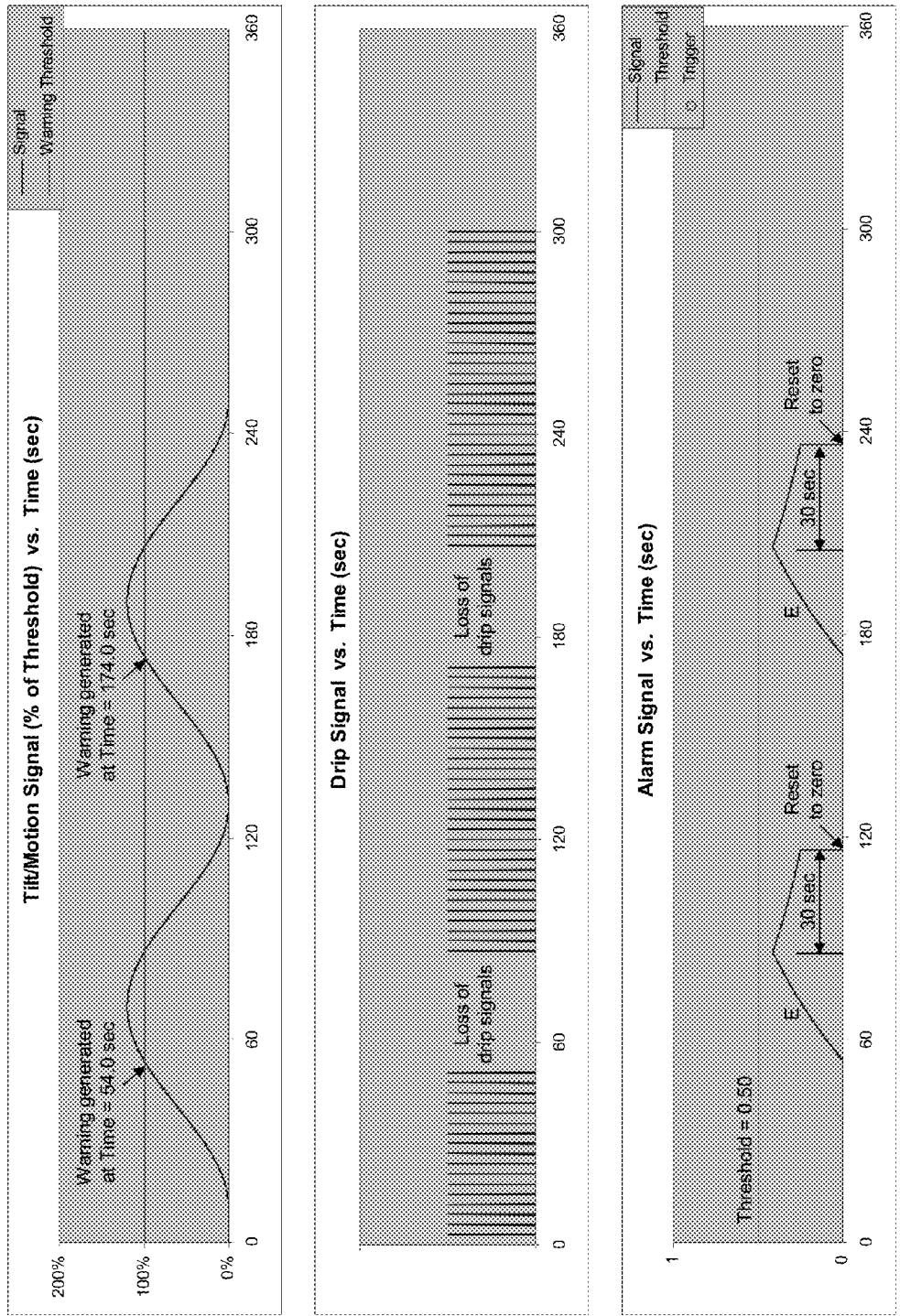
FIG. 9 shows another three graphs depicting another example tilt/motion situation, in accordance with an embodiment.

FIGS. 7-9 depict example graphs measuring tilt/motion signals, drip signals, and E parameters during three different example tilt events. Referring to FIG. 7, these three graphs depict an example situation in which the fluid delivery system is gradually tilted (or accelerated) until the alarm threshold is exceeded for a prolonged period of time. This causes the drip detection signals to vanish and an alarm to be generated.

As depicted in the top graph of FIG. 7, gradual tilting begins at 0 seconds. At 165.1 seconds, the tilt/motion signal exceeds the warning threshold and a warning condition is generated. As depicted in the middle graph of FIG. 7, the drip signals cease at 165.1 seconds as a result of the excessive tilting. However, the warning condition prevents the system from opening the valve in an effort to increase the flow rate. As depicted in the bottom graph of FIG. 7, an alarm condition is generated at 206.6 seconds, when the calculated value of E exceeds the threshold value, 0.5. The elapsed time from the beginning of the warning condition to the beginning of the alarm condition is 41.5 seconds. Upon alarming, the system would likely stop the flow due to absent drip signals.

Referring to FIG. 8, these three graphs depict an example situation in which the fluid delivery system experiences frequent cycles of tilting (or acceleration) that intermittently exceed their pre-established thresholds, causing intermittent losses of drip signals. As depicted in the top graph of FIG. 8, the tilt/motion of the system causes intermittent warnings, with the first of such warnings beginning at 15.2 seconds. As depicted in the middle graph of FIG. 8, the drip signals are lost during the warning periods, but the system is prevented from raising the flow rate. Finally, as depicted in the bottom graph of FIG. 8, the E parameter rises during the warning periods and falls between successive warning periods. The frequent tilt/motion cycling gives rise to a net rise of E over time. Once E exceeds the threshold value, 0.5, the system generates an alarm condition. This occurs at 184.8 seconds. The elapsed time from the beginning of the initial warning condition to the beginning of the alarm condition is 169.6 seconds. Upon alarming, the system would likely stop the flow due to absent drip signals.

Referring to FIG. 9, these three graphs depict an example situation in which the fluid delivery system experiences two identical tilt (or acceleration) events, each of which exceed their warning thresholds, causing a brief period of absent drip signals. As depicted in the top graph of FIG. 9, the first tilt/motion event causes a warning condition at about 54.0 seconds, and the second tilt/motion event causes a warning condition at about 174.0 seconds. Each tilt/motion event causes a brief interruption in the drip signals, as depicted in the middle graph of FIG. 9. And as depicted in the bottom graph of FIG. 9, the E value rises during the warning periods, but no alarm is generated because E never reaches the alarm threshold of 0.5. Furthermore, as depicted in the bottom graph of FIG. 9, the system resets the E parameter to zero after thirty seconds elapse following the end of a warning period. The first reset of E prevents the E parameter from exceeding the threshold during the second tilt/motion event due to carry-over from the first event, thus reducing the risk of a nuisance alarm.

Figure 10B:
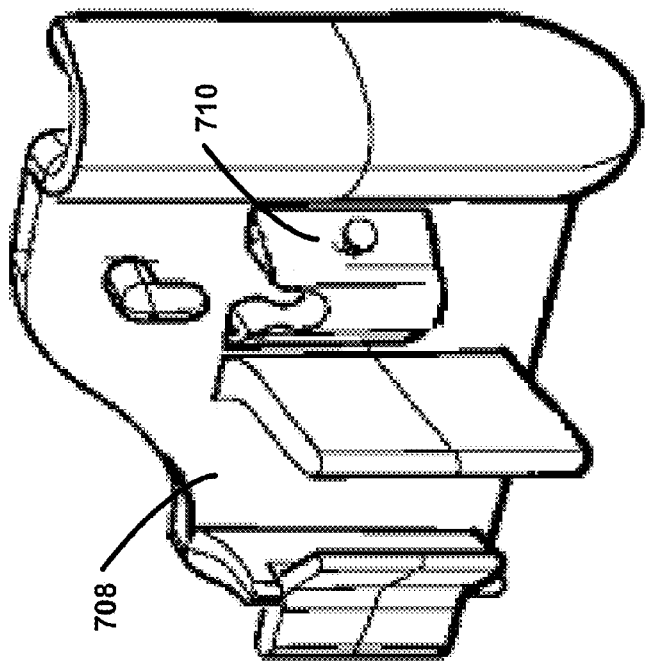
FIGS. 10A and 10B illustrate an example cradle, in accordance with an embodiment.
Figure 10A:
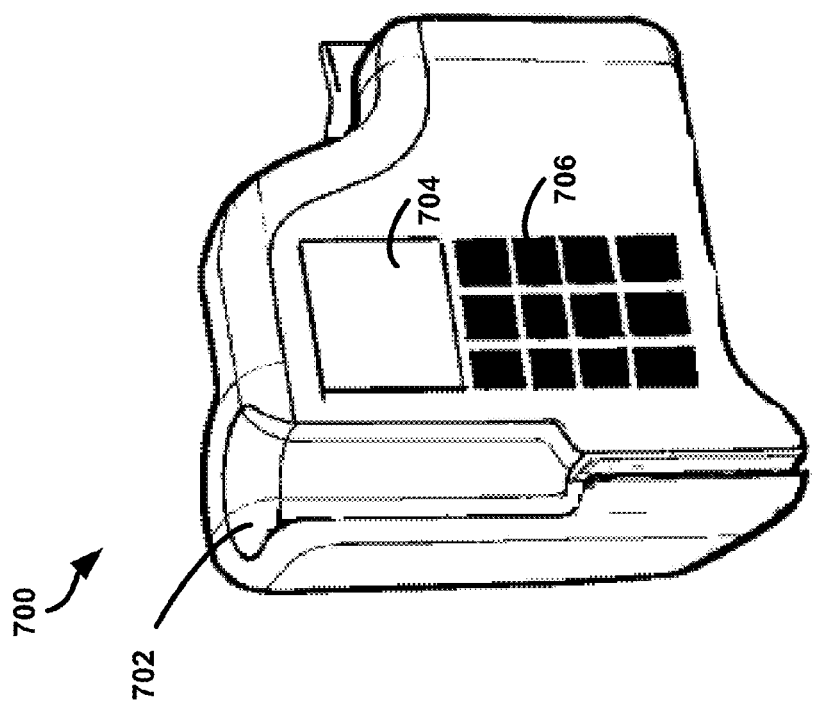

FIGS. 10A and 10B are illustrations of an example cradle 700 that may house at least some of the components of fluid delivery system 100, including (but not limited to) drip chamber 12, drip sensor 16, computing device 18, the imaging apparatus, the tilt detection element 44, etc. Cradle 700 includes a recessed portion 702 for releasably receiving drip chamber 12. Various components may be built into the wall of recessed portion 702 to aid in the detection and measurement of drops flowing through drip chamber 12. For example, parallel plates 42 may be built into the walls for detecting drops according to any method described above. At least part of the imaging apparatus, such as a camera, may be built into the walls of recessed portion 702 as well. Any remaining components (e.g., computing device 18, the tilt detection element 44, etc.) that aid in carrying out one or more of the methods described above may be built into the cradle elsewhere.

Cradle 700 may also include a display screen 704 (e.g., a liquid crystal display (LCD)) for displaying various information regarding the fluid delivery system 100. For instance, display 704 may, at times, display the measured dosage rate, the threshold (or desired) dosage rate, whether at least part of the system is in a tilted state, one or more alarms, or other information usually associated with fluid delivery systems. Buttons 706 may be used to manipulate the display 704 and control at least part of the computing device 18. For example, buttons 706, in conjunction with display 704, may be used to cycle the display on the screen, program a desired dosage rate, change a threshold angle for determining a tilted state, and do any number of other things.

Cradle 700 may include various means for attaching the cradle to a stationary object. Clamp 708 may be used to clamp the cradle 700 to a pole, whereas a strap (not shown) may attach to knob 710 to hang cradle 700 from a rod or hook. Other ways of attaching cradle 700 to a stationary object are certainly possible as well.

Figure 11B:
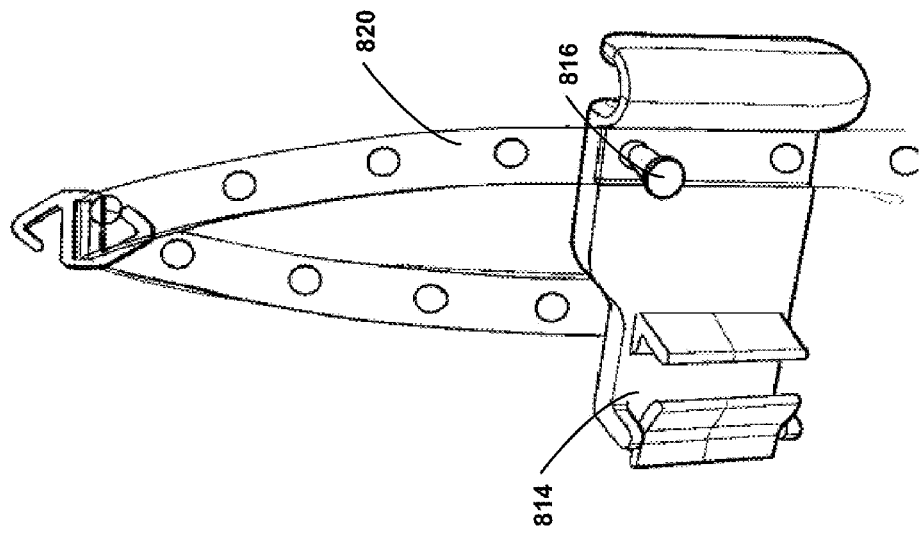
FIGS. 11A and 11B illustrate another example cradle, in accordance with an embodiment.
Figure 11A:
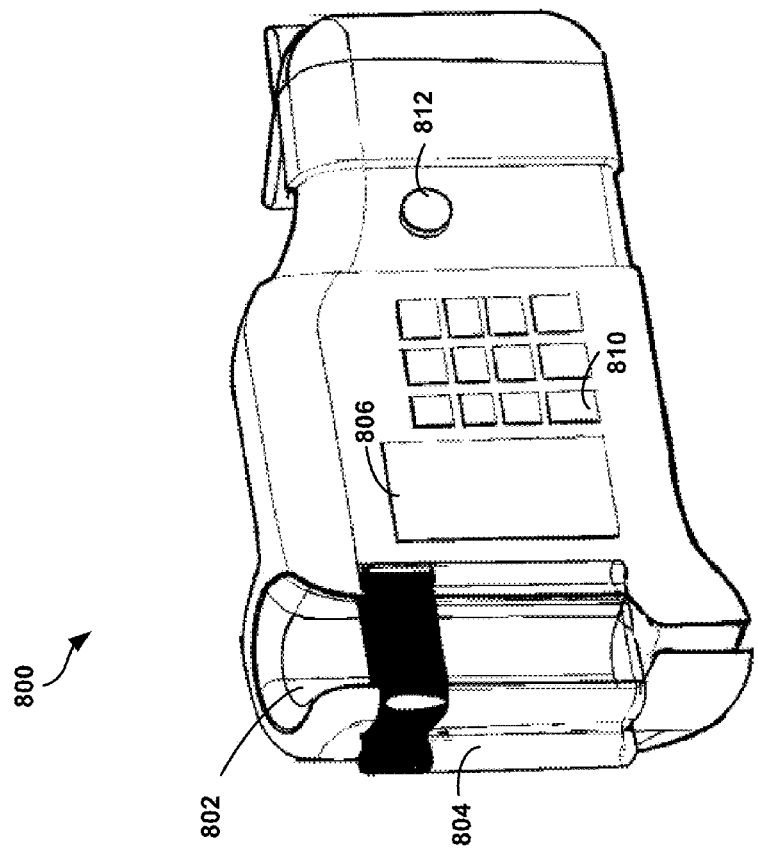

FIGS. 11A and 11B are illustrations of another example cradle 800 that may house at least some of the components of fluid delivery system 100, including (but not limited to) drip chamber 12, drip sensor 16, computing device 18, the imaging apparatus, one or more of the tilt detection element 44, etc. Cradle 800 includes a recessed portion 802 for releasably receiving drip chamber 12. Various components may be built into the wall of recessed portion 802 as well as any portion of cradle 800, such as those described above with respect to cradle 700.

Cradle 800 may include a door 804 for securing the drip chamber 12 into the recessed portion 802. If space is limited within the walls of recessed portion 802 or anywhere throughout cradle 800, any of the components described above may be built into the door 804, such as portions of drip sensor 16, portions of the imaging apparatus, portions of the tilt detection element 44, and/or portions of computing device 18.

Cradle 800 may also include a display screen 806 and buttons 810, such as those described above with respect to cradle 700. They may be used for carrying out similar functionality and therefore are not discussed further.

Cradle 800 may include various means for attaching the cradle to a stationary object. Clamp 814 may be used to clamp cradle 800 to a pole, whereas a strap 820 may attach to knobs 812 and 816 to hang cradle 800 from a rod or hook. Other ways of attaching cradle 800 to a stationary object are certainly possible as well.

Figure 12B:
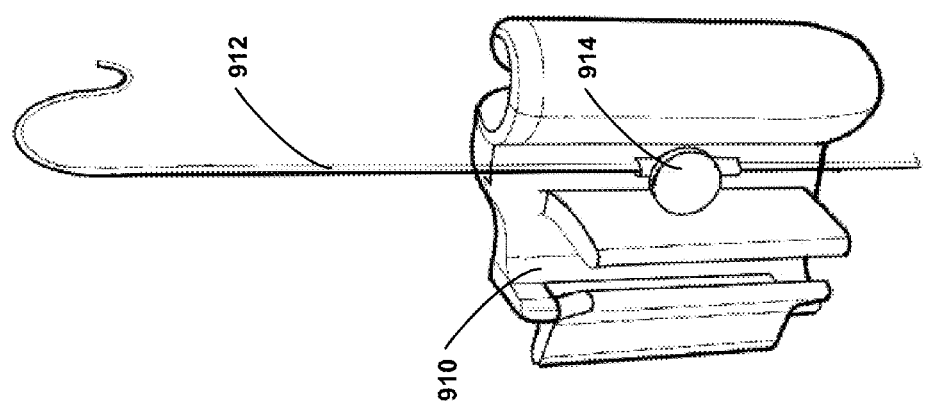
FIGS. 12A and 12B illustrate yet another example cradle, in accordance with an embodiment.
Figure 12A:
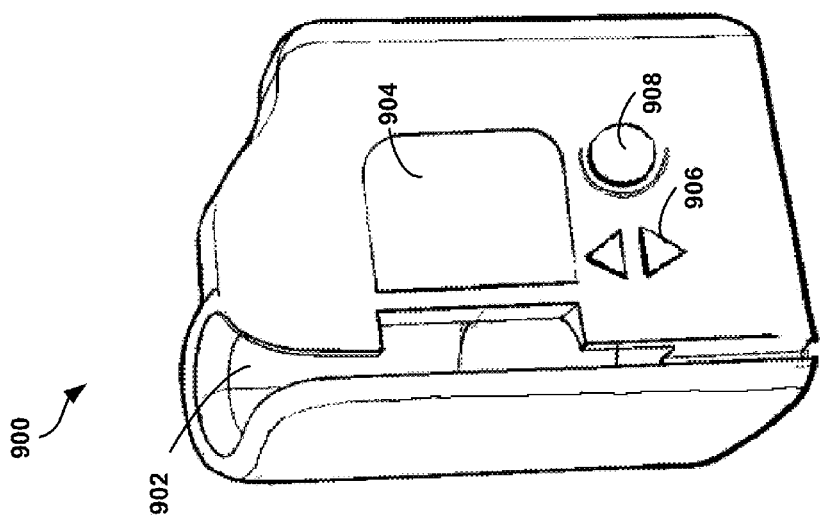

FIGS. 12A and 12B are illustrations of another example cradle 900 that may house at least some of the components of fluid delivery system 100, including (but not limited to) drip chamber 12, drip sensor 16, computing device 18, the imaging apparatus, one or more of the tilt detection element 44, etc. Cradle 900 includes a recessed portion 902 for releasably receiving drip chamber 12. The drip chamber 12 may be loaded into recessed portion 902 from the top of cradle 902 (i.e., top loaded) as opposed to loading drip chamber 12 into the recessed portion from the front of the cradle as may be the case with cradles 700 and 800, for example. Various components may be built into the wall of recessed portion 902 as well as any portion of cradle 900, such as those described above with respect to cradles 700 and 800.

Cradle 900 may also include a display screen 904, buttons 906, and a rotating dial 908, such as those described above with respect to cradles 700 and 800. They may be used for carrying out similar functionality and therefore are not discussed further.

Cradle 900 may include various means for attaching the cradle to a stationary object. Fastener 914 may be may be used to secure the cradle 900 to a pole 912, whereas clamp 910 may be used to clamp cradle 900 to a thicker pole (not shown). Other ways of attaching cradle 900 to a stationary object are certainly possible as well.

FIG. 13 is a block diagram illustrating an example of computing device 18 that may be associated with the system and method of the present application and may embody at least one computing device already described. The computing device 18 may perform at least one method step of the present application, for example.

In a very basic configuration 1001, computing device 18 typically includes one or more processors 1010 and system memory 1020. A memory bus 1030 can be used for communicating between the processor 1010 and the system memory 1020.

Depending on the desired configuration, processor 1010 can be of any type including but not limited to a microprocessor (µP), a microcontroller (µC), a digital signal processor (DSP), or any combination thereof. Processor 1010 can include one more levels of caching, such as a level one cache 1011 and a level two cache 1012, a processor core 1013, and registers 1014. The processor core 1013 can include an arithmetic logic unit (ALU), a floating point unit (FPU), a digital signal processing core (DSP Core), or any combination thereof. A memory controller 1015 can also be used with the processor 1010, or in some implementations the memory controller 1015 can be an internal part of the processor 1010.

Depending on the desired configuration, the system memory 1020 can be of any type including but not limited to volatile memory (such as RAM), non-volatile memory (such as ROM, flash memory, etc.) or any combination thereof. System memory 1020 typically includes an operating system 1021, one or more applications 1022, and program data 1024. For example, an application 1022 may be designed to receive certain inputs from drop sensor 16, a tilt detection element 44, an imaging apparatus, and/or any buttons described with reference to cradles 700, 800, or 900 and base decisions off of those inputs in accordance with at least some of the described methods. As an output, the application 1022 may carry out any of the methods described herein above and provide various electrical signals to various components of fluid delivery system 100 in accordance with the methods described herein.

Computing device 18 can have additional features or functionality, and additional interfaces to facilitate communications between the basic configuration 1001. For example, a bus/interface controller 1040 can be used to facilitate communications between the basic configuration 1001 and one or more data storage devices 1050 via a storage interface bus 1041. The data storage devices 1050 can be removable storage devices 1051, non-removable storage devices 1052, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media can include volatile and nonvolatile, removable and non-removable media implemented in any method or technology for storage of information, such as computer readable instructions, data structures, program modules, or other data.

System memory 1020, removable storage 1051 and non-removable storage 1052 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 18. Any such computer storage media can be part of device 18.

Computing device 18 can also include an interface bus 1042 for facilitating communication from various interface devices to the basic configuration 1001 via the bus/interface controller 1040. Example output interfaces 1060 include a graphics processing unit 1061 and an audio processing unit 1062, which can be configured to communicate to various external devices such one of the display screens described above with reference to cradles 700, 800, or 900, or speakers via one or more A/V ports 1063. Example peripheral interfaces 1060 include a serial interface controller 1071 or a parallel interface controller 1072, which can be configured to communicate with external devices such as input devices (e.g., keyboard, mouse, pen, voice input device, touch input device, buttons described above with reference to cradles 700, 800, or 900, etc.) or other peripheral devices (e.g., printer, scanner, etc.) via one or more I/O ports 1073. An example communication interface 1080 includes a network controller 1081, which can be arranged to facilitate communications with one or more other computing devices 1090 over a network communication via one or more communication ports 1082. The Communication connection is one example of a communication media. Communication media may typically be embodied by computer readable instructions, data structures, program modules, or other data in a modulated data signal, such as a carrier wave or other transport mechanism, and includes any information delivery media. A "modulated data signal" can be a signal that has one or more of its characteristics set or changed in such a manner as to encode information in the signal. By way of example, and not limitation, communication media can include wired media such as a wired network or direct-wired connection, and wireless media such as acoustic, radio frequency (RF), infrared (IR) and other wireless media. The term computer readable media (or medium) as used herein can include both storage media and communication media.

Computing device 18 can be embedded in one of cradles 700, 800, or 900, implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 18 can also be implemented as a personal computer including both laptop computer and non-laptop computer configurations.

Various examples of a fluid delivery system, drop detection and volume determinations, flow rate adjustment operations, computing devices, and cradles have been described above. Those skilled in the art will understand, however, that changes and modifications may be made to those examples without departing from the scope of the claims.

We claim:

1. An apparatus for determining a rate of fluid flow in a fluid delivery system comprising a drip chamber and a length of tubing, the apparatus comprising:
   a. a cradle configured to receive the drip chamber;
   b. a valve configured to receive the length of tubing and to control a rate of fluid flow through the length of tubing; and
   c. a flow rate determination element configured to determine a flow rate of fluid passing through the drip chamber, the flow rate determination element comprising, a camera for imaging activity within the drip chamber, a computing device, a memory storage coupled to the computing device, and a set of software instructions stored in the memory storage which when executed by the computing device causes the apparatus to carry out functions, the functions comprising:
   detecting a presence of a drop of fluid falling within the drip chamber;
   in response to the detecting, triggering the camera to capture a first image of the drip chamber with the drop falling therein;
   capturing a second image of the drip chamber with no drop falling therein;
   eliminating splash effects from the first image of the drip chamber by subtracting from the first image portions of the second image that appear in substantially the same position in each of the first and second images in order to create a drop image that is substantially free of splash effects; and
   determining a volume of the drop based on the drop image.

2. The apparatus of claim 1, wherein determining the volume of the drop comprises:
   computationally rotating the drop image about an axis; and
   determining a volume of a shape resulting from the computationally-rotated drop image.

3. The apparatus of claim 1, wherein detecting the presence of the drop in the drip chamber comprises:
   detecting a change in a signal received from a detector having two electrically conductive metal plates, the change in the signal resulting from the presence of a drop within the drip chamber.

4. The apparatus of claim 3, wherein the cradle comprises a door operable between an open position in which the drip chamber can be placed into or removed from the cradle and a closed position in which the drip chamber is secured within the cradle, and wherein one of the two electrically conductive metal plates is mounted on the door.

5. The apparatus of claim 3, wherein the camera is positioned substantially perpendicularly to the metal plates.

6. The apparatus of claim 1, wherein the functions further comprise:
   repeating the functions for successive drops detected in the drip chamber for a predetermined period of time; and
   summing the determined volumes of drops falling within the drip chamber to generate a volume sum and dividing the volume sum by the predetermined amount of time to generate a flow rate for the predetermined amount of time.

7. The apparatus of claim 1, wherein detecting the presence of the drop in the drip chamber comprises:
   detecting a change in a signal received from a beam emitter and a beam detector.

8. The apparatus of claim 7, wherein the cradle comprises a door operable between an open position in which the drip chamber can be placed into or removed from the cradle and a closed position in which the drip chamber is secured within the cradle, and wherein one of the beam emitter and beam detector is mounted the door.

9. A method for determining a flow rate of fluid delivered by a fluid delivery system, the fluid delivery system including a drip chamber, the method comprising:
   detecting a presence of a drop in the drip chamber;
   in response to the detecting, capturing a first image of the drip chamber and the drop falling therein;
   capturing a second image of the drip chamber with no drop falling therein;
   eliminating splash effects from the first image of the drip chamber by subtracting from the first image any portions of the second image that appear in substantially the same position in both the first and second images in order to create a drop image that is substantially free of splash effects; and
   determining a volume of the drop based on said drop image.

10. The method of claim 9, wherein detecting a presence of a drop in the drip chamber comprises:
    detecting a change in a signal received from a detector having two electrically conductive metal plates, the change in the signal resulting from the presence of a drop within the drip chamber.

11. The method of claim 9, wherein detecting a presence of a drop in the drip chamber comprises:

detecting a change in a signal received from a beam emitter and a beam detector.

12. The method of claim 9, wherein the second image is captured after the first image is captured.

13. The method of claim 9, wherein the second image is captured before the first image is captured.

14. The method of claim 9, further comprising:
for successive detected drops over a predetermined period of time, repeating the preceding steps of detecting, capturing a first image, capturing a second image, eliminating splash effects, and determining a volume; and
summing the determined volumes of successive detected drops and dividing the sum by the predetermined period of time to provide a flow rate.

15. An apparatus for determining a rate of fluid flow in a fluid delivery system comprising a drip chamber and a length of tubing, the apparatus comprising:
a. a cradle configured to receive the drip chamber;
b. a valve configured to receive the length of tubing and to control a rate of fluid flow through the length of tubing; and
c. a flow rate determination element configured to determine a flow rate of fluid passing through the drip chamber, the flow rate determination element comprising, a camera for imaging activity within the drip chamber, a computing device, a memory storage coupled to the computing device, and a set of software instructions stored in the memory storage which when executed by the computing device causes the apparatus to carry out functions, the functions comprising:
detecting a presence of each one of a plurality of drops of fluid falling within the drip chamber;
in response to the detection of each drop, triggering the camera to capture a first image of the drip chamber with the drop falling therein;
for each captured first image of the drip chamber, capturing a corresponding second image of the drip chamber with no drop falling therein;
subtracting from the first image portions of the corresponding second image that appear in substantially the same position in each of the first and second images in order to create a drop image for each drop; and
determining a volume of each drop based on the drop image created for the drop.

16. The apparatus of claim 15, wherein the second image is captured after the first image is captured.

17. The apparatus of claim 15, wherein the second image is captured before the first image is captured.

18. The apparatus of claim 15, wherein the detecting the presence of each one of the plurality of drops of fluid falling within the drip chamber comprises detecting all drops falling within the drip chamber over a predetermined period of time.

19. The apparatus of claim 18, wherein the functions further comprise determining a flow rate of fluid passing through the drip chamber by:
determining a volume sum by summing the volumes determined for each drop; and
dividing the volume sum by the predetermined period of time.

20. The apparatus of claim 15, wherein the functions further comprise failing to detect at least one drop falling within the drip chamber.

* * * * *